(12) United States Patent
Xu

(10) Patent No.: US 8,883,138 B2
(45) Date of Patent: Nov. 11, 2014

(54) ADIPONECTIN PRODUCTION ACCELERATING COMPOSITION

(75) Inventor: Shanhua Xu, Eniwa (JP)

(73) Assignee: Final Future International, Inc., Aichi (JP)

( * ) Notice: Subject to any disclaimer, the term of this patent is extended or adjusted under 35 U.S.C. 154(b) by 0 days.

(21) Appl. No.: 13/261,517

(22) PCT Filed: May 13, 2011

(86) PCT No.: PCT/JP2011/002678
§ 371 (c)(1),
(2), (4) Date: Nov. 16, 2012

(87) PCT Pub. No.: WO2011/145307
PCT Pub. Date: Nov. 24, 2011

(65) Prior Publication Data
US 2013/0089532 A1 Apr. 11, 2013

(30) Foreign Application Priority Data
May 21, 2010 (JP) ................. 2010-117264

(51) Int. Cl.
| | | |
|---|---|---|
| A61K 36/064 | (2006.01) | |
| A61K 33/30 | (2006.01) | |
| A61K 45/06 | (2006.01) | |
| A61K 33/34 | (2006.01) | |
| A61K 31/7105 | (2006.01) | |
| A61K 35/60 | (2006.01) | |
| A61K 33/04 | (2006.01) | |
| A61K 38/39 | (2006.01) | |
| A61K 36/06 | (2006.01) | |

(52) U.S. Cl.
CPC ............... *A61K 38/39* (2013.01); *A61K 33/30* (2013.01); *A61K 45/06* (2013.01); *A61K 36/064* (2013.01); *A61K 33/34* (2013.01); *A61K 31/7105* (2013.01); *A61K 35/60* (2013.01); *A61K 33/04* (2013.01); *A61K 36/06* (2013.01)
USPC ....................................................... 424/93.51

(58) Field of Classification Search
USPC ....................................................... 424/93.51
See application file for complete search history.

(56) References Cited

U.S. PATENT DOCUMENTS

| 2002/0132773 A1 | 9/2002 | Kincade et al. | |
| 2004/0076690 A1* | 4/2004 | Ikemoto et al. | 424/729 |
| 2006/0057254 A1* | 3/2006 | Kojima et al. | 426/74 |

FOREIGN PATENT DOCUMENTS

| EP | 1908455 | * | 4/2008 | ............... A61K 8/84 |
| JP | 08-238072 A1 | | 9/1996 | |
| JP | 09-224607 A | | 9/1997 | |
| JP | 11-290025 A | | 10/1999 | |
| JP | 3018186 B1 | | 1/2000 | |
| JP | 2000-256208 A | | 9/2000 | |
| JP | 2002-363094 A | | 12/2002 | |
| JP | 2004-016143 A | | 1/2004 | |
| JP | 2005-232059 A | | 9/2005 | |
| JP | 2005-325072 A | | 11/2005 | |
| JP | 2006-045210 A | | 2/2006 | |
| JP | 2006-056836 A | | 3/2006 | |
| JP | 2008-063293 A | | 3/2008 | |
| JP | 2009-063293 A | | 3/2008 | |
| JP | 2008063293 | * | 3/2008 | ............... A23L 1/03 |
| JP | 2010-037221 A | | 2/2010 | |
| JP | 2010-088403 A | | 4/2010 | |

OTHER PUBLICATIONS

Liu et al. Relative chromium response as an indicator of chromium status. The American Journal of Clinical Nutrition. 1978;31:972-976.*
Saiga-Egusa et al. Antihypertensive effects and endothelial progenitor cell activation by intake of chicken collagen hydrolysate in pre- and mild-hypertension. Biosci. Biotechnol. Biochem. 2009;73:422-424.*
Hussein et al. Astaxanthin ameliorates features of metabolic syndrome in SHR/NDmcr-cp. Life Sciences. 2007;80:522-529.*
Brewer Yeast. Brewer's Yeast. Lewis Laboratories International, Ltd. 2003;1-3.*
VirtualMart. Nutra-Kol food NutraPlus micro feed 125ml. VirtualMart. 2008;1-3.*
Arita et al., "Paradoxical Decrease of an Adipose-Specific Protein, Adiponectin, in Obesity," Biochemical and Biophysical Research Communications, 1999, 257:79-83.
Baba et al., "Studies on *Angelica Keiskei* 'Asitaba'," Foods Food Ingredients J. Jpn., 1998, 178:52-60, with English summary on first page.

(Continued)

*Primary Examiner* — Ruth Davis
*Assistant Examiner* — Lynn Y Fan
(74) *Attorney, Agent, or Firm* — Foley & Lardner LLP

(57) ABSTRACT

A problem to be solved is to provide an orally ingestible composition which promotes the production of adiponectin and which is free from safety issues such as side effects and toxicity. An adiponectin production promoting composition is prepared which comprises salmon milt extract, brewer's yeast extract, avian collagen, and yeast containing mineral and having an adiponectin production promoting activity. Preferably, the salmon milt extract comprises low molecular weight components obtained by enzymatic degradation of salmon milt into oligonucleotides and oligopeptides. Preferably, the brewer's yeast extract comprises 50 to 80% of RNA. Preferably, the mineral yeast comprises, in dry yeast, 2 to 3% of zinc, 0.3 to 0.5% of copper, and 0.01 to 0.02% of selenium. Preferably, the adiponectin production promoting composition comprises 16 to 17 parts by mass of the brewer's yeast extract, 33 to 34 parts by mass of the avian collagen, and 22 to 23 parts by mass of the yeast containing mineral per 100 parts by mass of the salmon milt extract.

4 Claims, 1 Drawing Sheet

(56) References Cited

OTHER PUBLICATIONS

Maeda et al., "cDNA Cloning and Expression of a Novel Adipose Specific Collagen-like Factor, apM1 (Adipose Most Abundant Gene Transcript 1)," Biochemical and Biophysical Research Communications, 1996, 221:286-289.

Miyano et al., "Clinical Application of Nucleic Acid Nutritional Therapy to Dogs and Cats," Journal of Japanese Society of Traditional Veterinary Medicine, 1999, 5:57-60, with partial English translation.

* cited by examiner

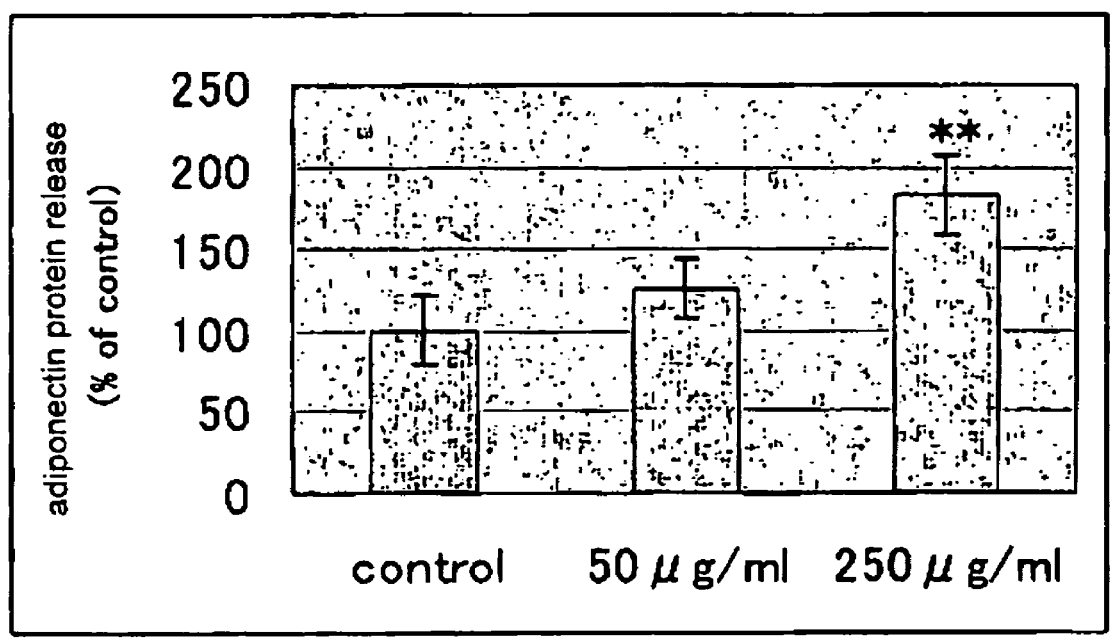

ADIPONECTIN PRODUCTION ACCELERATING COMPOSITION

CROSS-REFERENCE TO RELATED APPLICATIONS

This application is a National Stage application of PCT/JP2011/002678, filed May 13, 2011, which claims priority from Japanese application JP 2010-117264, filed May 21, 2010.

TECHNICAL FIELD

The present invention relates to a composition which promotes the production of adiponectin, and more particularly to an adiponectin production promoting agent consisting of salmon milt extract, brewer's yeast extract, avian collagen (chicken collagen), and yeast containing mineral (containing Zn, Se, and Cu).

BACKGROUND ART

Adiponectin is a hormone consisting of 244 amino acids, which is secreted from adipose tissue. It was isolated from human adipose tissue in 1996. It is a secretory protein specific for adipose tissue (Non-patent Document 2), and it is present not only in adipose tissue but also in blood in a large amount (5 to 10 μg/ml in healthy people) (Non-patent Document 3). It is known to promote fat burning and uptake of sugar in skeletal muscle and liver by activating AMP kinase (AMP-activated protein kinase: AMPK). It is known that this adiponectin is secreted in a large amount from small adipocytes; however, the secretion volume decreased with the enlargement of adipocytes.

Adiponectin is also known as a beneficial adipocytokine, which suppresses arteriosclerosis. Regarding adipocytokines, in addition to the aforementioned beneficial adipocytokines, there are harmful adipocytokines such as PAI-1 and TNF-α, which promote arteriosclerosis. In a normal state, the secretion volumes of beneficial and harmful adipocytokines are balanced. However, when adipocytes are enlarged due to obesity and the like, the secretion volume of beneficial adipocytokines decreased, whereas harmful adipocytokines are secreted in excess. As a result, the balance between these adipocytokines is disturbed, presumably leading to the development of lifestyle-related diseases such as type II diabetes mellitus and arteriosclerosis.

As described above, adiponectin is associated with obesity and lifestyle-related diseases caused by obesity, and it is assumed that activation of this adiponectin is effective for the prevention or treatment of lifestyle-related diseases. Further, adiponectin is also known to have an inhibitory effect on hepatic fibrosis. Adiponectin has been shown to have a wide variety of actions such as improvement of hypertension, fat metabolism, and insulin sensitivity, an anti-inflammatory action, suppression of hepatic fibrosis, a facilitatory effect on the proliferation of normal hepatocytes (Patent Document 1), and an anti-inflammatory effect (Patent Document 2) (Patent Documents 2 to 5), suggesting that a drug, drink, or food which increases the blood concentration of adiponectin has a preventive or amelioratingactivity on metabolic syndrome.

Under such a background, a thiazolidine derivative is known as a drug promoting the production of adiponectin. However, this thiazolidine derivative may cause side effects such as digestive symptoms such as diarrhea, constipation, and queasy feeling as well as hepatic dysfunction.

Furthermore, some compounds or components which promote the production of adiponectin are proposed. For example, Patent Document 6 discloses that N-acetylcysteine increases the expression level of adiponectin in adipocytes, and apocynin increases the plasma concentration of adiponectin and also the expression level of adiponectin in adipose tissue. Patent Document 7 discloses that a gingerol compound enhances the production of adiponectin, and Patent Document 8 discloses that amla fruit or its extract enhances the production of adiponectin. Besides these, excellent adiponectin production promoting substances are still demanded. Accordingly, under present circumstances in which countermeasures against metabolic syndrome have become a social issue, development of a safe substance which has an action of promoting and enhancing in vivo production of adiponectin has been demanded.

PRIOR ART DOCUMENTS

Patent Documents

Patent Document 1: Japanese unexamined Patent Application Publication No. 2002-363094
Patent Document 2: Japanese unexamined Patent Application Publication No. 2000-256208
Patent Document 3: Japanese Patent No. 3018186
Patent Document 4: U.S. Patent Application Publication No. 2002/0132773
Patent Document 5: Japanese unexamined Patent Application Publication No. 2005-325072
Patent Document 6: Japanese unexamined Patent Application Publication No. 2005-232059
Patent Document 7: Japanese unexamined Patent Application Publication No. 2006-45210
Patent Document 8: Japanese unexamined Patent Application Publication No. 2006-56836

Non-Patent Documents

Non-patent Document 1: Kimie Baba et al., Foods & Food Ingredients Journal of Japan, No. 178, pp. 52 to 60 (1998)
Non-patent Document 2: Maeda K et al., Biochem. Biophys. Res. Commun., 221: 286 (1996)
Non-patent Document 3: Arita Y et al., Biochem. Biophys. Res. Commun., 257: 79 to 83 (1999)

SUMMARY OF THE INVENTION

Object to be Solved by the Invention

An object of the present invention is to provide an orally ingestible composition which promotes the production of adiponectin and which is free from safety issues such as side effects and toxicity.

Means to Solve the Object

The present inventor has studied a variety of food raw materials for adiponectin production. As a result, she has found that a mixture prepared by combining salmon milt extract, brewer's yeast extract, avian collagen (chicken collagen), and yeast containing mineral (containing Zn, Se, and Cu) exhibits excellent adiponectin production promoting ability, thereby completing the present invention.

That is, the present invention relates to [1] an adiponectin production promoting composition comprising salmon milt extract, brewer's yeast extract, avian collagen, and yeast containing mineral and having an adiponectin production promoting activity, [2] the adiponectin production promoting composition according to [1], wherein the salmon milt extract comprises low molecular weight components obtained by treating salmon milt with enzyme to degrade into oligonucleotides and oligopeptides, [3] the adiponectin production promoting composition according to [1] or [2], wherein the brewer's yeast extract comprises 50 to 80% of RNA, [4] the adiponectin production promoting composition according to any one of [1] to [3], wherein the mineral yeast comprises, 2 to 3% of zinc, 0.3 to 0.5% of copper, and 0.01 to 0.02% of selenium in dried yeast, and [5] the adiponectin production promoting composition according to any one of [1] to [4], wherein the composition comprises 16 to 17 parts by the mass of brewer's yeast extract, 33 to 34 parts by mass of the avian collagen, and 22 to 23 parts by mass of the yeast containing mineral per 100 parts by mass of the salmon milt extract.

Effect of the Invention

The adiponectin production promoting agent of the present invention is mainly composed of salmon milt extract. Although none of brewer's yeast extract, avian collagen, and yeast containing mineral is known to have adiponectin producibility by itself alone, these substances attain an excellent facilitatory effect on the production of adiponectin when mixed together. The adiponectin production promoting agent of the present invention is effective for the improvement, treatment, or prevention of diabetes mellitus, obesity, arteriosclerosis, symptoms attributable to these diseases such as complications of diabetes mellitus (such as diabetic retinopathy, diabetic neuropathy, and diabetic nephropathy), cerebral infarction, myocardial infarction, and renal sclerosis.

BRIEF DESCRIPTION OF DRAWINGS

FIG. 1 is a graph showing the results of measurement of the concentration of adiponectin secreted in the culture supernatant of adipocytes using the adiponectin production promoting composition of the present invention.

MODE OF CARRYING OUT THE INVENTION

The adiponectin production promoting composition of the present invention is not particularly limited as long as it is a composition which comprises salmon milt extract, brewer's yeast extract, avian collagen, and yeast containing mineral, and which has an adiponectin production promoting activity. Here, the adiponectin production promoting activity refers to an activity of promoting the secretion of adiponectin, which is an important regulatory factor for sugar metabolism, fat metabolism, and the like, and increasing the amount of adiponectin in the body, particularly in blood.

Although the aforementioned salmon milt extract is not particularly limited as long as it can be used as food, salmon milt extract comprising low molecular weight components are obtained by enzymatic degradation of salmon milt into oligonucleotides and oligopeptides, is preferable. Particularly, salmon milt extract comprising oligonucleotides having a molecular weight of 1000 to 3000 and 20 to 70% of oligopeptides is preferable. Such salmon milt extract can be obtained from, for example, L•S Factory Co., Ltd.

Further, the aforementioned salmon milt extract can also be prepared in accordance with the method described in Japanese unexamined Patent Application Publication No. 2004-16143. That is, after removing the skin, stringy tissue, vein, and the like from salmon milt, the resulting milt is de-oiled by purification, and then treated with protease and nuclease. The aforementioned protease is mainly composed of trypsin. Trypsin is a highly specific serine protease, which selectively hydrolyzes the peptide bond at the carboxyl side of arginine and lysine. Thus, it is suitable for hydrolysis of arginine-rich protamine. Also, the aforementioned protease can also comprise, in addition to trypsin, other proteases such as chymotrypsin. Examples of favorable proteases can include proteases manufactured by Novo Nordisk Bioindustry Ltd. Also, the temperature at which a hydrolysis reaction by nuclease is performed is in a range of 60 to 75° C., among which 70° C. is most preferable. Although the order of protease treatment and nuclease treatment is not particularly limited, it is preferable to perform protease treatment first, followed by nuclease treatment.

Although the aforementioned brewer's yeast extract is not particularly limited as long as it can be used as food, brewer's yeast extract comprising 50 to 80% of RNA is preferable. Such brewer's yeast extract can be obtained from, for example, L•S Factory Co., Ltd.

Although the aforementioned avian collagen (chicken collagen) is not particularly limited, one which is used as food is preferably used. Preferable examples can include avian collagen manufactured by L•S Factory Co., Ltd.

Although the aforementioned mineral yeast is not particularly limited as long as it is baker's yeast with increased mineral content, one comprising, in dry yeast, 2 to 3% of zinc is preferable, and among such yeast, mineral yeast comprising, in dry yeast, 2 to 3% of zinc, 0.3 to 0.5% of copper, and 0.01 to 0.02% of selenium can be used. Such mineral yeast can be obtained from L•S Factory Co., Ltd and the like. Also, such mineral yeast can be prepared by mixing zinc yeast with high zinc content, copper yeast with high copper content, and selenium yeast with high selenium content. Each of the aforementioned yeast with high mineral content can be obtained from L•S Factory Co., Ltd and the like.

Also, with regard to the mixing ratio of salmon milt extract, brewer's yeast extract, avian collagen, and yeast containing mineral in the adiponectin production promoting composition of the present invention, preferable examples can include a composition comprising 10 to 25 parts by mass, preferably 16 to 17 parts by mass of the brewer's yeast extract, 25 to 40 parts by mass, preferably 33 to 34 parts by mass of the avian collagen, and 15 to 30 parts by mass, preferably 22 to 23 parts by mass of the yeast, containing mineral, per 100 parts by mass of salmon milt extract.

The adiponectin production promoting composition of the present invention may contain various additional components for the formulation, such as a conventional pharmaceutically acceptable carrier, binder, stabilizer, excipient, diluent, pH buffering agent, disintegrant, solubilizing agent, solubilizing aid, or isotonic agent, or be used in combination with a therapeutic drug such as other adiponectin production promoting agents.

The adiponectin production promoting composition of the present invention can be used as a pharmaceutical product, a supplement, food, feed, etc. which are useful for treating or preventing diseases caused by decreased adiponectin production. The daily dose or intake amount per adult is preferably 0.1 to 10 g, more preferably 0.5 to 5 g.

The kind of the food products or food raw materials to which the adiponectin production promoting composition of the present invention is applicable is not particularly limited. Examples thereof can include a variety of drinks such as yogurt, a yogurt drink, juice, milk, soy milk, alcohols, coffee, tea, sencha (green tea), oolong tea, and a sport drink, bread and confectionery such as baked confectionery such as pudding, cookies, bread, cake, jelly, and a rice cracker, Japanese traditional confectionery such as yokan (sweet jellied azuki bean paste), chilled or frozen confectionery, and chewing gum, noodles such as udon (noodles made from wheat flour) and soba (noodles made from buckwheat), a processed fish paste product such as kamaboko (solidified fish paste), ham, and fish meat sausage, seasonings such as miso (soy bean paste), soy sauce, dressing, mayonnaise, and a sweetener, a dairy product such as cheese and butter, tofu, konjac jelly, and also, a variety of ready-to-eat food products such as tsukudani (sweetened food materials boiled down in soy sauce), dumplings, croquette, and salad. Also, to the food products and food raw materials to which the adiponectin production promoting composition has been applied, other nutritional components such as vitamins and minerals can be further mixed as needed. When the adiponectin production promoting composition of the present invention is applied to a food product or feed, the package or attached instruction leaflet of the food product or food raw material, feed or feed raw material can display that the product has an adiponectin production promoting activity.

Hereinbelow, the present invention will be specifically described with reference to Examples; however, the technical scope of the present invention is not limited by these Examples.

EXAMPLES

Example 1

[Sample Preparation]

In PBS, 60 mg of salmon milt extract ("Nuclegen" manufactured by L•S Factory Co., Ltd), 10 mg of brewer's yeast extract ("Brewer's yeast extract RNA" manufactured by L•S Factory Co., Ltd), 20 mg of collagen ("Chicken collagen" manufactured by L•S Factory Co., Ltd), and 13.5 mg of yeast containing mineral ("Mix mineral yeast C" manufactured by L•S Factory Co., Ltd) were suspended and prepared at 2.5 mg/ml, and the resulting solution was filtered through a 0.45 µm pore size filter. Using the filtrate thus obtained, samples were evaluated at the concentrations shown in Table 1.

TABLE 1

| Component | Sample 1 (µg/ml) | Sample 2 (µg/ml) | Sample 3 (µg/ml) |
|---|---|---|---|
| Salmon milt extract | 0 | 29 | 145 |
| Brewer's yeast extract | 0 | 4.8 | 24 |
| Collagen | 0 | 9.7 | 48.5 |
| Yeast containing mineral | 0 | 6.5 | 32.5 |
| Total | 0 | 50 | 250 |

[Facilitatory Effect on the Production of Adiponectin]
(1) Culture and Subculture of 3T3-L1 Cells After culturing 3T3-L1 cells (mouse fibroblast cells) in a 10% newborn calf serum-containing Dulbecco's Modified Eagle's Medium (CS-DMEM) to confluency, the medium in the culture flask was removed, followed by washing with PBS (−) twice. Subsequently, cells were detached from the bottom of the flask by adding a 0.1% trypsin-EDTA solution, and the detached cells and 0.1% trypsin-EDTA solution were transferred to a centrifugation tube. To this, an equal amount of 10% CS-DMEM was added, followed by centrifugation at 1500 rpm for five minutes. Subsequently, cells were homogenized in 10% FCS-DMEM, seeded in a flask, and then placed in a $CO_2$ incubator. The cells were then cultured under the condition of 5% $CO_2$ at 37° C.

(2) Differentiation Induction into Adipocytes

The 3T3-L1 cells were cultured in 10% CS-DMEM, and two days after the cells reached confluency, the medium was exchanged for a differentiation medium 1, followed by further two days of culture. Subsequently, the medium was exchanged for a differentiation medium 2, followed by further two days of culture. For differentiation induction into adipocytes, the differentiation media 1 and 2 were used.

The differentiation medium 1 is DMEM supplemented with 10% FBS, 0.5 mM isobutyl-1-methylxanthine (IBMX), 1 µM dexamethasone (DEX), and 10 µg/ml insulin. The differentiation medium 1 was prepared by diluting a mixture of 10 mg/ml insulin, 500 mM IBMX, and 1 mM DEX with 10% FCS-DMEM. Also, the differentiation medium 2 is DMEM supplemented with 10% FCS and 1 µM insulin. The differentiation medium 2 was prepared by diluting 10 mg/ml insulin with 10% FCS-DMEM.

(3) Evaluation of the Facilitatory Effect on the Production of Adiponectin

After differentiation into adipocytes, the medium was exchanged for 0.1% BSA-DMEM, followed by 24 hours of culture. Subsequently, the mixture was added so that the concentration was 0 µg/ml (Sample 1), 50 µg/ml (Sample 2), or 250 µg/ml (Sample 3), followed by further incubation at 37° C. for 48 hours. The culture supernatant was collected and the amount of adiponectin in the supernatant was measured by the adiponectin ELISA kit (Otsuka Pharmaceutical Co., Ltd.). The results thus obtained are shown in FIG. 1, and numerically expressed results are shown in Table 2.

As a result, compared to mixture-free (Sample 1), samples with 50 µg/ml and 250 µg/ml mixture showed a concentration-dependent increase in the concentration of adiponectin. Setting the mixture-free sample (control) at 100%, the concentrations of adiponectin secreted in the culture supernatant in the samples with 50 µg/ml and 250 µg/ml mixture were 126% and 183%, respectively, relative to the control (with a significant difference with a significance level of 1%). In this experiment, the viability was not affected at any concentration.

TABLE 2

| | Amount of adiponectin production (% of Control) |
|---|---|
| Sample 1 (0 µg/ml): Control | 100% |
| Sample 2 (50 µg/ml) | 126% |
| Sample 3 (250 µg/ml) | 183% |

Example 2

An orally-administered adiponectin production promoting agent (tablet) was prepared by mixing salmon milt extract ("Nuclegen" manufactured by L•S Factory Co., Ltd), brewer's yeast extract ("Brewer's yeast extract RNA" manufactured by L•S Factory Co., Ltd), collagen ("Chicken collagen" manufactured by L•S Factory Co., Ltd), yeast containing mineral ("Mix mineral yeast C" manufactured by L•S Factory Co., Ltd) at the ratio shown in Table 3, and adding other vitamins.

TABLE 3

| Component | In 6 tablets |
| --- | --- |
| Salmon milt extract | 600 mg |
| Brewer's yeast extract | 100 mg |
| Collagen | 200 mg |
| Yeast containing mineral | 135 mg |

INDUSTRIAL APPLICABILITY

The adiponectin production promoting agent of the present invention promotes the secretion of adiponectin, which is an important regulatory factor for sugar metabolism, fat metabolism, and the like, whereby increasing the amount of adiponectin in the body, particularly in blood. The adiponectin production promoting agent of the present invention is effective for the improvement, treatment, or prevention of diabetes mellitus, obesity, arteriosclerosis, and symptoms attributable to these diseases such as complications of diabetes mellitus (such as diabetic retinopathy, diabetic neuropathy, and diabetic nephropathy), cerebral infarction, myocardial infarction, and renal sclerosis. The adiponectin production promoting composition (adiponectin production promoting agent) of the present invention can be used as a pharmaceutical product, a supplement, food, and so on.

The invention claimed is:

1. An adiponectin production promoting composition comprising a salmon milt extract comprising oligonucleotides having a molecular weight of 1000 to 3000 and 20 to 70% oligopeptides, a brewer's yeast extract comprising 50 to 80% RNA, avian collagen, and yeast containing mineral, wherein the composition comprises 16 to 17 parts by mass of the brewer's yeast extract per 100 parts of mass of the salmon milt extract, 33 to 34 parts by mass of the avian collagen per 100 parts by mass of the salmon milt extract, and 22 to 23 parts by mass of the yeast containing mineral per 100 parts by mass of the salmon milt extract, and wherein the composition has an adiponectin production promoting-activity.

2. The adiponectin production promoting composition according to claim 1, wherein the salmon milt extract comprises low molecular weight components obtained by treating salmon milt with enzyme to degrade into oligonucleotides and oligopeptides.

3. The adiponectin production promoting composition according to claim 1, wherein the mineral yeast comprises, 2 to 3% of zinc, 0.3 to 0.5% of copper, and 0.01 to 0.02% of selenium in dried yeast.

4. The adiponectin production promoting composition according to claim 2, wherein the mineral yeast comprises, 2 to 3% of zinc, 0.3 to 0.5% of copper, and 0.01 to 0.02% of selenium in dried yeast.

* * * * *

UNITED STATES PATENT AND TRADEMARK OFFICE
CERTIFICATE OF CORRECTION

PATENT NO. : 8,883,138 B2  Page 1 of 1
APPLICATION NO. : 13/261517
DATED : November 11, 2014
INVENTOR(S) : Shanhua Xu It is certified that error appears in the above-identified patent and that said Letters Patent is hereby corrected as shown below:

In the Claims

Col. 8, claim 1, line 8, "100 parts of mass of" should be --100 parts by mass of--.

Signed and Sealed this
Sixteenth Day of June, 2015

Michelle K. Lee
*Director of the United States Patent and Trademark Office*